United States Patent
Luhmann

(10) Patent No.: US 9,872,709 B2
(45) Date of Patent: Jan. 23, 2018

(54) SPINAL CORRECTION CONSTRUCT AND METHOD

(71) Applicant: Warsaw Orthopedic, Inc., Warsaw, IN (US)

(72) Inventor: Scott J. Luhmann, St. Louis, MO (US)

(73) Assignee: Warsaw Orthopedic, Inc., Warsaw, IN (US)

(*) Notice: Subject to any disclaimer, the term of this patent is extended or adjusted under 35 U.S.C. 154(b) by 147 days.

(21) Appl. No.: 14/285,974

(22) Filed: May 23, 2014

(65) Prior Publication Data

US 2015/0335358 A1 Nov. 26, 2015

(51) Int. Cl.
*A61B 17/70* (2006.01)

(52) U.S. Cl.
CPC ...... *A61B 17/7014* (2013.01); *A61B 17/7004* (2013.01)

(58) Field of Classification Search
CPC ............ A61B 17/7002; A61B 17/7014; A61B 17/7016; A61B 17/7017
USPC .................................. 606/246, 258–260, 90
See application file for complete search history.

(56) References Cited

U.S. PATENT DOCUMENTS

| 4,573,454 | A | 3/1986 | Hoffman |
| 6,554,831 | B1 | 4/2003 | Rivard et al. |
| 2010/0106192 | A1 | 4/2010 | Barry |
| 2010/0160967 | A1* | 6/2010 | Capozzoli .......... A61B 17/7011 606/256 |
| 2011/0184463 | A1 | 7/2011 | Schwend |
| 2011/0270314 | A1 | 11/2011 | Mueller et al. |
| 2012/0271353 | A1* | 10/2012 | Barry .................. A61B 17/705 606/258 |
| 2012/0310285 | A1 | 12/2012 | Zhao et al. |
| 2013/0150889 | A1* | 6/2013 | Fening ............... A61B 17/7022 606/257 |

FOREIGN PATENT DOCUMENTS

CN 2011684005 U 12/2010

* cited by examiner

*Primary Examiner* — Ellen C Hammond
*Assistant Examiner* — Christina Negrellirodrigue

(57) ABSTRACT

A spinal construct comprises a connector defining a longitudinal axis and extending between a first end and a second end. The connector defines a cavity and includes a member that is selectively disposable in the cavity at one of a plurality of positions between the ends. A first longitudinal element is dynamically movable within the cavity and engageable with the member to limit movement in a first axial direction. The first longitudinal element is connectable with vertebral tissue. A second longitudinal element is disposable within the cavity and connectable with vertebral tissue. Systems and methods are disclosed.

19 Claims, 3 Drawing Sheets

SPINAL CORRECTION CONSTRUCT AND METHOD

TECHNICAL FIELD

The present disclosure generally relates to medical devices for the treatment of musculoskeletal disorders, and more particularly to a surgical system and a method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants such as rods, tethers and bone screws for stabilization of a treated section of a spine. This disclosure describes an improvement over these prior art technologies.

SUMMARY

In one embodiment, a spinal construct is provided. The spinal construct comprises a connector defining a longitudinal axis and extending between a first end and a second end. The connector defines a cavity and includes a member that is selectively disposable in the cavity at one of a plurality of positions between the ends. A first longitudinal element is dynamically movable within the cavity and engageable with the member to limit movement in a first axial direction. The first longitudinal element is connectable with vertebral tissue. A second longitudinal element is disposable within the cavity and connectable with vertebral tissue. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
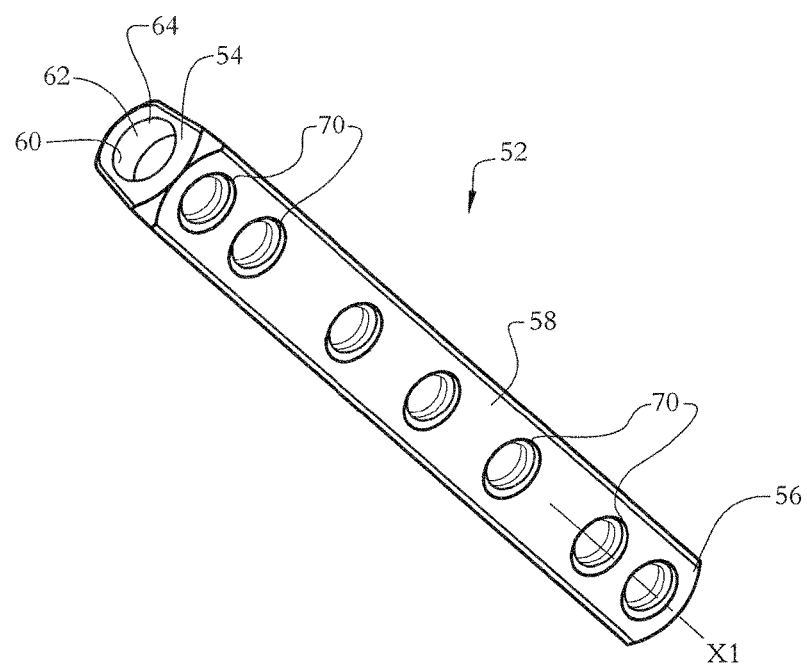
FIG. 1 is a perspective view of components of one embodiment of a system in accordance with the principles of the present disclosure.

The exemplary embodiments of the system and related methods of use disclosed are discussed in terms of medical devices for the treatment of musculoskeletal disorders and more particularly, in terms of a surgical system and method for treatment of a spine disorder.

In some embodiment, the present system and method can be employed to treat severe scoliosis in a growing child and utilize spinal construct, which may include, for example, growing rods, vertical expandable prosthetic titanium rib, Shilla technique components, vertebral body stapling and/or tethers. In some embodiments, the present system and method can include limitations based on type and magnitude of spinal deformity effectively treated, age of a patient, and underlying co-morbidities, which may impact outcome.

In one embodiment, the system includes a spinal construct having a connector configured to distract a spine across a spinal deformity. In one embodiment, the spinal construct includes a connector configured to provide a distraction force including a tension with the use of multiple rods. In one embodiment, the spinal construct includes a connector configured for use with side-to-side domino connectors and/or longitudinal axial connectors.

In one embodiment, the spinal construct includes a dynamic axial connector that allows for micro-motion of a growth rod in rotation and/or axial translation while preventing collapse and/or shortening of the growth rod. In one embodiment, the spinal construct includes a connector configured to lessen spine stiffness and/or minimize premature auto-fusion due to dynamic motion of the spinal construct. In one embodiment, the spinal construct includes a connector configured to reduce forces on the spinal construct. This configuration can reduce the number of revision surgeries and increase interval time between revisions.

In some embodiments, the system includes a spinal construct having a connector configured to facilitate distraction of a spine across a region of spinal deformity, similar to pulling rope. In one embodiment, the spinal construct is configured to apply a distraction force and have the intrinsic ability to place tension on the spine with the use of overlapping rods with side-to-side domino connectors or with longitudinal axial connectors.

In one embodiment, the spinal construct includes a connector configured to provide a distraction force to the spine and then to maintain this force by preventing collapse of the system, such as, for example, loss of the distraction force. In one embodiment, the spinal construct includes a connector configured to facilitate axial pistoning of a rod within the connector to dissipate axial forces, in one embodiment, the spinal construct includes a connector configured to dissipate rotational forces of circular spinal rods.

In one embodiment, the spinal construct includes a connector configured to minimize friction and generation of metallic particulates by utilizing a highly polished rod and inner surface of the connector. In one embodiment, interaction of the polished surfaces allows for micro-motion, such as, for example, arthroplasty, while minimizing production of wear debris. In one embodiment, the spinal construct includes a connector configured to maintain a two-dimensional angular alignment at the completion of surgery. In one embodiment, the spinal construct includes a connector having holes for blocking screws. In one embodiment, the holes are milled into a top slot of the connector.

In one embodiment, the system includes a spinal construct having a connector that includes blocking screws. In one embodiment, the spinal construct includes a connector having blocking screws that are long enough to block axial collapse of the construct. In one embodiment, the spinal construct includes a connector having a slot with screw holes defined that allow for a rod distractor to be used with lengthening procedures. In one embodiment, the spinal construct includes a connector configured for use with a rod implanted for the treatment of juvenile and/or infantile scoliosis.

In one embodiment, the present system can be employed with a method that includes selecting a cephalad and caudad foundation site. In one embodiment, the method includes the step of placing spinal fixation points, such as, for example, screws, hooks and wires at the foundation sites. In one embodiment, the method includes the step of placing a spinal construct on a concave side first followed by a convex side. In one embodiment, the method includes the step of determining the optimal location of the connector, such as, for example, can be disposed at a thoraco-lumbar junction due the connector having a straight configuration. In one embodiment, the method includes the step of placing the connector caudally if there is kyphosis at the thoraco-lumbar junction. In one embodiment, the method includes the step of placing the connector in the paraspinal space near midline.

In one embodiment, the method includes the step of measuring sections of spinal rods from a middle of the connector to the proximal and distal foundations. In one embodiment, the method includes the step of providing extra rod length to permit tensioning of the construct, for example, to not use the connector at the initial construct implantation. In one embodiment, the method includes the step of implanting a longer rod segment if an initial rod on a concave side is too short after tensioning of the construct.

In some embodiments, the spinal construct includes two rod segments, cephalad and caudad, being contoured to the patient's spinal deformity. In some embodiments, the method includes the step of placing the segments of the rods into the connector in a straight configuration without any bend. In one embodiment, the method includes the step of inserting one of the rod segments into a receiver of a bone fastener and securing by tightening set screws. In one embodiment, the method includes the step of inserting the implanted first rod segment with the connector. In one embodiment, the method includes the step of inserting a second rod segment into the connector and securing into its corresponding bone fastener with a set screw. In one embodiment, the system includes a single dynamically movable spinal rod such that to prevent axial translation of the connector, one of the rod segments is rigidly fixed with the connector by use of a locking set screw. In one embodiment, to prevent axial translation of the connector, a single blocking screw is disposed between the two ends of the rod segments thereby providing for two dynamic spinal rods.

In one embodiment, the method includes the step of tensioning the spinal construct by distracting against the proximal, distal or both foundation or by using the connector. In one embodiment, the method includes the step of placing an opposite side rod such as, for example, a convex side in the same manner. In one embodiment, the method includes the step of determining the length of a rod to be disposed within the connector. In some embodiments, the present system is configured such that the two rod segments are fully inside the connector to optimize the number of scheduled lengthening that can be performed without needing to revise the construct. In one embodiment, the method includes the step of loosening one or both of the rod segments at the foundation and slid into the connector and re-tensioned by distracting against that particular foundation. In one embodiment, the spinal construct shortens the spine with the other rod fixed in place with the desired distraction.

In some embodiments, the present system can be employed with a method such that the length of each of the rods, projecting cephalad and caudad from its respective foundation, can be assessed and trimmed. In some embodiments, the present system can be employed with a method such that a thoracolumbar-sacral orthosis can be used for a period of time, such as, for example, six months after implantation of the spinal construct. In one embodiment, the present system can be employed with a method such that lengthening intervals are used, such as, for example, six month lengthening intervals.

In some embodiments, one or all of the components of the present system may be disposable, peel-pack, pre-packed sterile devices. One or all of the components of the system may be reusable. The system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, vessels, ligaments, tendons, cartilage and/or bone unless specifically referred to otherwise.

Figure 2:
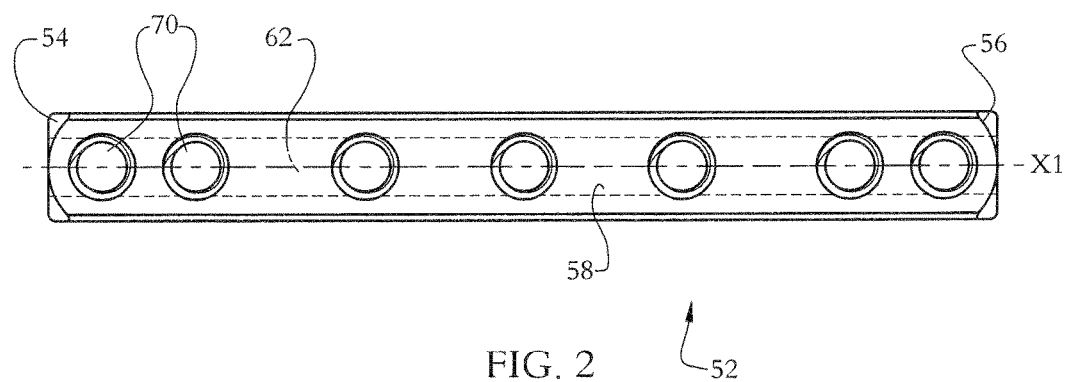
FIG. 2 is a side view of the components shown in FIG. 1.
Figure 3:
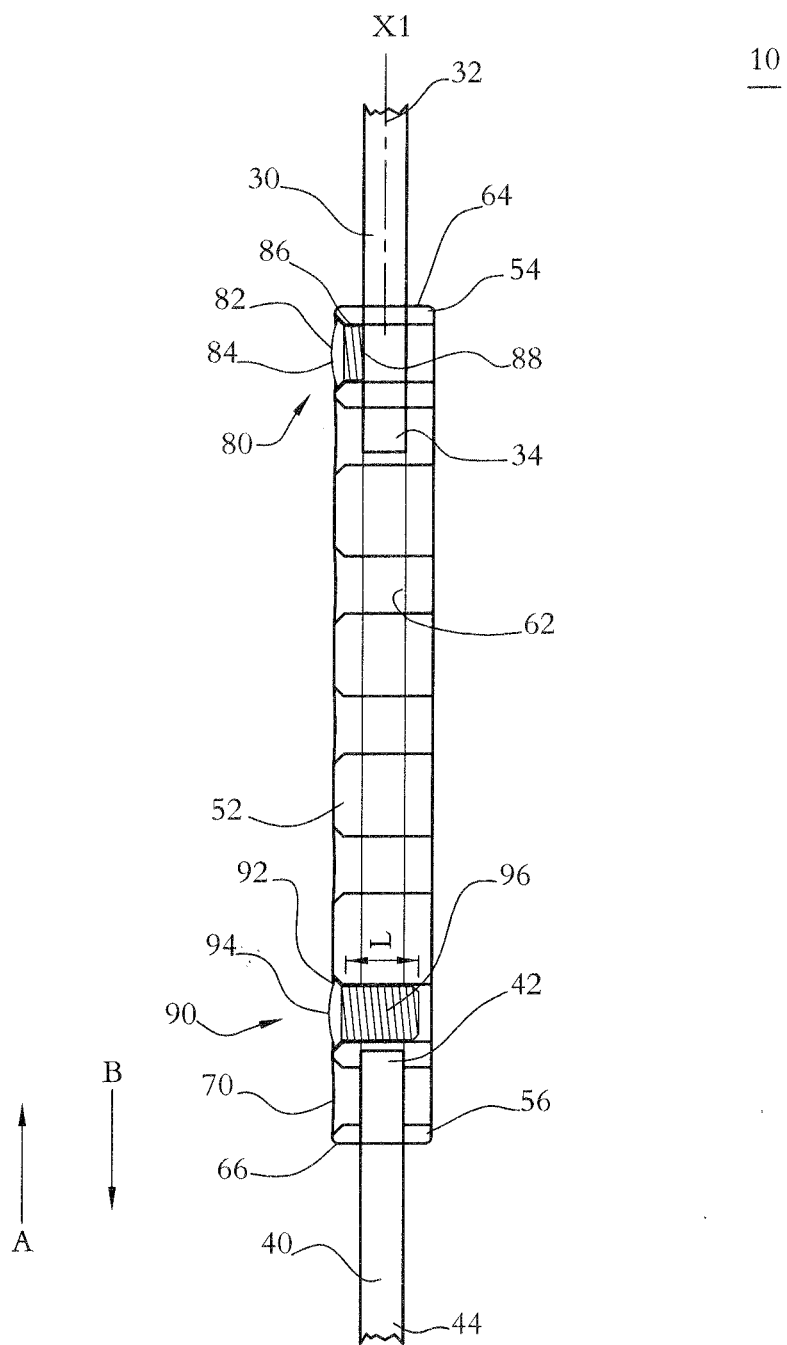
FIG. 3 is a cross section view of components of one embodiment of a system in accordance with the principles of the present disclosure.

The following discussion includes a description of a surgical system including surgical instruments, related components and methods of employing the system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a system, such as, for example, a surgical correction system 10 in accordance with the principles of the present disclosure.

The components of system 10 can be fabricated from biologically acceptable materials suitable for medical applications, including metals, synthetic polymers, ceramics and bone material and/or their composites. For example, the components of system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL' manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

Spinal correction system 10 is employed, for example, with an open or mini-open, minimal access and/or minimally invasive including percutaneous surgical technique and includes one or more spinal constructs for a correction treatment at a surgical site within a body of a patient, for example, a section of a spine to treat various spine pathologies, such as, for example, adolescent idiopathic scoliosis and Scheuermann's kyphosis. In one embodiment, the components of spinal correction system 10 are configured to deliver and introduce an implant, such as, for example, a spinal construct that includes one or more spinal rods, connectors and fasteners. The spinal construct forms one or more components of a correction treatment and/or correction system used for positioning and alignment for stabilization of a treated section of vertebrae, which is implanted with the vertebrae.

Figure 4:
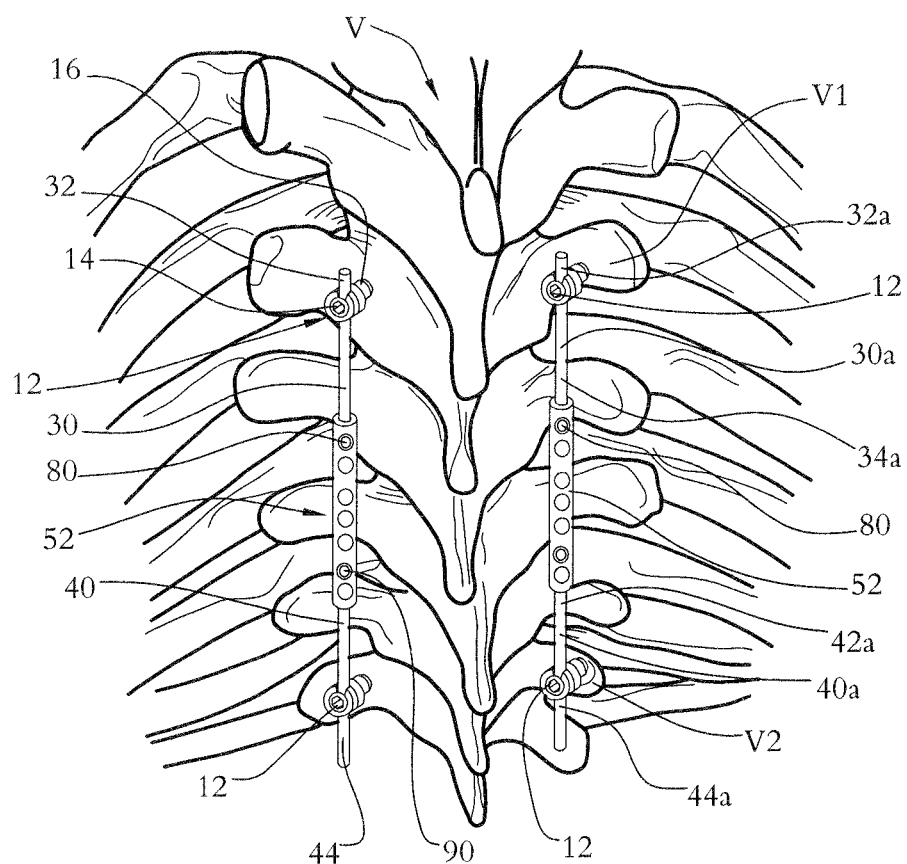
FIG. 4 is a plan view of components of one embodiment of a system in accordance with the principles of the present disclosure disposed with vertebrae.

In one embodiment, the spinal construct includes a fastener, such as, for example, a bone screw 12 that is fixed with vertebrae V, as shown in FIG. 4. In some embodiments, the spinal construct may include one or a plurality of fasteners. In some embodiments, one or more of bone screws 12 may be engaged with tissue in various orientations, such as, for example, series, parallel, offset, staggered and/or alternate vertebral levels, in some embodiments, one or more fasteners may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

Bone screw 12 comprises a portion, such as, for example, a head 14 and a portion, such as, for example, an elongated shaft 16 configured for penetrating tissue. Head 14 includes a receiving portion configured for disposal of a longitudinal element, such as, for example, a spinal rod, for example, a rod 30 and/or a rod 40. Rods 30, 40 are attached with and extend along a posterior portion of vertebrae V.

Rod 30 extends between an end 32 and an end 34. Rod 40 extends between an end 42 and an end 44. Rod 30 and/or 40 can have a uniform thickness/diameter. In some embodiments, rod 30 and/or 40 may have various surface configurations, such as, for example, rough, threaded for connection with surgical instruments, arcuate, undulating, dimpled, polished and/or textured. In some embodiments, a thickness defined by rod 30 and/or rod 40 may be uniformly increasing or decreasing, or have alternate diameter dimensions along their length. In some embodiments, rod 30 and/or rod 40 may have various lengths.

In some embodiments, the spinal construct includes a connector 52, as shown in FIGS. 1 and 2, which defines a longitudinal axis X1. Connector 52 extends between an end 54 and an end 56. Connector 52 has a rectangular cross section configuration. In some embodiments, connector 52 may have an oval, oblong, triangular, square, polygonal, irregular, uniform, non-uniform, offset, staggered, undulating, arcuate, variable and/or tapered configuration. Connector 52 includes an outer surface 58. In some embodiments, all or only a portion of outer surface 58 may have alternate surface configurations such as, for example, rough, arcuate, undulating, mesh, porous, semi-porous, dimpled and/or textured.

Connector 52 includes an inner surface 60 that defines a cavity, such as, for example, a longitudinal passageway 62. Passageway 62 extends axially along connector 52. Passageway 62 is configured for disposal of one or more spinal rods and relative axial translation of the spinal rod(s) relative to connector 52. Passageway 62 has a circular cross section configuration. In some embodiments, passageway 62 may have alternate cross sectional configurations for disposal of alternately shaped spinal rods, such as, for example, oval, oblong, triangular, square, polygonal, irregular, uniform, non-uniform, offset, undulating, arcuate, variable and/or tapered. In some embodiments, inner surface 60 may define cross section configurations different from the cross section of one or more spinal rods disposed within passageway 62 such that connector 52 may limit, resist and/or prevent rotational movement of the one or more spinal rods relative to connector 52.

Passageway 62 includes an opening 64 adjacent end 54 and an opening 66 adjacent end 56. In one embodiment, opening 64 is configured for movable disposal of rod 30, discussed herein. In one embodiment, opening 66 is configured for moveable disposal of rod 40, discussed herein. In some embodiments, openings 64, 66 may have alternate cross sectional configurations for disposal of alternately shaped spinal rods, as described herein. In some embodiments, opening 64 and/or opening 66 may limit, resist and/or prevent rotational movement in at least one direction of a spinal rod disposed therewith relative to connector 52.

Outer surface 58 defines plurality of spaced apart openings 70 that communicate with a threaded portion of surface 60. Each opening 70 is configured to receive a member, such as, for example, screw 80 that is threaded with surface 60 for engagement of screw 80 with a spinal rod. Openings 70 are each in communication with passageway 62 such that screw 80 can be oriented to engage a spinal rod. In some embodiments, engagement of screw 80 with a spinal rod can include a fixation with an outer surface of the spinal rod to fix the rod with connector 52 and/or abutting engagement of screw 80 with an end of a spinal rod to limit, resist and/or prevent movement of the rod relative to connector 52. In one embodiment, openings 70 include a buttress thread to facilitate engagement with screw 80.

Screw 80 includes a surface 82 having a socket 84. Socket 84 is configured for engagement with an instrument (not shown), as described herein, to secure screw 80 with a spinal rod and connector 52. Screw 80 includes a threaded shaft 86 configured for engagement with the threaded portion of surface 60 adjacent openings 70. Shaft 86 includes an end surface 88 configured to engage an outer surface of a spinal rod to fix, such as, for example, rod 30 with connector 52 and resist and/or prevent movement of rod 30 relative to connector 52. In some embodiments, screw 80 can be configured to abut an end of rod 30 to limit, resist and/or prevent axial movement in at least one direction of rod 30 relative to connector 52. In some embodiments, a fastener engages an outer surface of rod 40 to fix rod 40 with connector 52 and resist and/or prevent movement of rod 40 relative to connector 52.

A member, such as, for example, a screw 90 is selectively disposable in one of openings 70 at one of a plurality of positions between ends 54, 56. Screw 90 is engageable with an end of a spinal rod to limit, resist and/or prevent axial movement in an axial direction, in the direction shown by arrow A in FIG. 3, of, for example, rod 40 relative to connector 52. Screw 90 includes a surface 92 including a socket 94. Socket 94 is configured for engagement with an instrument (not shown), as described herein, Screw 90 includes a threaded shaft 96 configured for engagement with the threaded portion of surface 60 adjacent openings 70.

Shaft 96 includes a length L such that shaft 96 extends into passageway 62 to engage, block and/or abut a spinal rod, such as, for example, end 42 of rod 40 to limit, resist and/or prevent axial movement of rod 40 in an axial direction, in the direction shown by arrow A, relative to connector 52 along axis X1 and allow axial translation of rod 40 in an axial direction, in the direction shown by arrow B, along axis X1 in a dynamically movable configuration, as described herein. In some embodiments, screw 90 can be alternately disposable in one of the plurality of openings 70 to engage, block and/or abut a spinal rod at a selective position along connector 52 to adjust a range of movement of the spinal rod in a dynamically movable configuration, as described herein.

In some embodiments, a single screw 90 is selectively disposed in one of openings 70 at one of a plurality of positions between ends 54, 56. End 34 is dynamically axially translatable and/or dynamically rotatable within passageway 62 adjacent end 54 and relative to connector 52. End 42 is dynamically axially translatable and/or dynamically rotatable within passageway 62 adjacent end 56 and relative to connector 52. Screw 90 is engageable with each of ends 34, 42. Shaft 96 extends into passageway 62 to engage, block and/or abut end 34 to limit, resist and/or prevent axial movement of rod 30 in a first axial direction relative to connector 52 along axis X1 and allow dynamic axial translation of rod 30 in a second opposing axial direction. Shaft 96 extends into passageway 62 to engage, block and/or abut end 42 to limit, resist and/or prevent axial movement of rod 40 in the second axial direction relative to connector 52 along axis X1 and allow dynamic axial translation of rod 40 in the first axial direction. This configuration can prevent axial migration of connector 52 while maintaining a dynamically movable configuration of rods 30, 40. In some embodiments, rod 30 and/or rod 40 may include a dynamically axially translatable configuration, as described herein, and connector 52 may be configured, as described herein, such that connector 52 may limit, resist and/or prevent rotational movement in at least one direction of rod 30 and/or rod 40 relative to connector 52.

In some embodiments, rod 30 and/or rod 40 are connected with heads 14 of bone screws 12 causing a tension in rods 30, 40 and/or vertebrae V. In some embodiments, the spinal construct, for example, rods 30, 40 and/or a tension thereof is employed to displace, pull, twist or align vertebrae V as part of a correction system and treatment. In one embodiment, end 32 of rod 30 is fixed with at least one vertebra and end 34 is dynamically moveable within passageway 62. In one embodiment, end 44 of rod 40 is fixed with at least one vertebra and end 42 is dynamically moveable within passageway 62, as described herein. In one embodiment, end 32 of rod 30 is fixed with at least one vertebra and end 34 is dynamically rotatable within passageway 62. In one embodiment, end 44 of rod 40 is fixed with at least one vertebra and end 42 is dynamically rotatable within passageway 62, as described herein. In one embodiment, end 34 comprises a member that extends into passageway 62 to engage, block and/or abut end 42 to limit, resist and/or prevent axial movement of rod 40 in a first axial direction relative to connector 52 along axis X1 and allow dynamic axial translation of rod 40 in a second opposing axial direction.

In some embodiments, rod 30 and/or rod 40 has a flexible configuration, which includes movement in a lateral or side to side direction and prevents expanding and/or extension in an axial direction upon fixation with vertebrae. In some embodiments, all or only a portion of rod 30 and/or rod 40 may have a semi-rigid, rigid, flexible or elastic configuration, and/or have elastic and/or flexible properties such as the elastic and/or flexible properties corresponding to the material examples described herein. Rod 30 and/or rod 40 can include a plurality of separately attachable or connectable portions or sections, such as bands or loops, or may be monolithically formed as a single continuous element.

In assembly, operation and use, as shown in FIG. 4, spinal correction system 10, similar to the systems and methods described herein, is employed with and/or subsequent to a surgical correction procedure employing a surgical correction system, similar to those described herein. In some embodiments, spinal correction system 10 may be employed concurrently with the surgical correction procedure. For example, spinal correction system 10 may be employed in surgical procedures for treating disorders of the spine, such as, for example, a correction treatment to treat child/adolescent idiopathic scoliosis and/or Scheuermann's kyphosis of a spine. In some embodiments, one or all of the components of system 10 can be delivered as a pre-assembled device or can be assembled in situ.

The surgical correction treatment includes a spinal construct used for correction and alignment for stabilization of a treated section of vertebrae V. In use, to create tension along vertebrae V with rods 30, 40, a medical practitioner obtains access to a surgical site including vertebrae V via a posterior surgical approach. In some embodiments, the surgical site may be accessed in any appropriate manner, such as through incision and retraction of tissues. In some embodiments, system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area.

Pilot holes are made in vertebrae V1, V2 on a concave side of vertebrae V. Bone screws 12, as described herein, are aligned with the pilot holes and fastened with the tissue of vertebrae V1, V2. End 32 of rod 30 is fixed with bone screw 12 disposed with vertebra V1. End 34 is disposed within passageway 62 of connector 52 adjacent end 54. End 42 of rod 40 is disposed within passageway 62 adjacent end 56. End 44 is fixed with bone screw 12 disposed with vertebra V2. Rods 30, 40 are manipulated to a desired tensioning along vertebrae V to displace, pull, twist or align vertebrae V as part of a correction system and treatment.

Screw 80 is selectively positioned with one of openings 70 adjacent end 54. Screw 80 is threaded with surface 60 for engagement of screw 80 with end 34 of rod 30. Socket 84 is engaged with a surgical driver (not shown) to secure screw 80 with rod 30 and connector 52. End surface 88 engages an outer surface of rod 30 to rigidly fix rod 30 with connector 52 and resist and/or prevent movement of rod 30 relative to connector 52.

Screw 90 is selectively disposed in one of openings 70 at one of a plurality of positions between ends 54, 56. Socket 94 is engaged with a surgical driver (not shown) such that shaft 96 extends into passageway 62 to engage, block and/or abut end 42 of rod 40 to limit, resist and/or prevent axial movement of rod 40 in an axial direction, in the direction shown by arrow A in FIG. 3, relative to connector 52 along axis X1 and allow axial translation of rod 40 in an axial direction, in the direction shown by arrow B, along axis X1 in a dynamically movable configuration. End 42 is dynamically axially translatable and dynamically rotatable relative to connector 52 within passageway 62. End 42 has a range of dynamic axial movement between the surface of shaft 96 within passageway 62 and an end-most surface of end 56 that supports rod 40. In some embodiments, the components of system 10, such as, for example, connector 52 and/or rods 30, 40, are configured to provide dynamically responsive movement in response to motion of the spine and adjacent anatomical portions due to factors, such as, for example, growth, trauma, aging, natural load bearing and dynamic characteristics of the spine, which may include flexion, extension, rotation and lateral bending, and/or external loads, which may include axial, shear, linear, non-linear, angular, torsional, compressive and/or tensile loads applied to the body of a patient.

In some embodiments, as shown in FIG. 4, spinal correction system 10 comprises a bilateral spinal construct. The bilateral spinal construct comprises a first connector 52 attached with rods 30, 40 and connected with a concave side of vertebrae V, as described above. The bilateral spinal construct also comprises a second connector 52 similarly attached with spinal rods 30*a*, 40*a*, similar to rods 30, 40 described herein, and similarly connected with a convex side of vertebrae V.

In some embodiments, spinal correction system 10 includes an agent, for example, which may be disposed, packed, coated or layered within, on or about the components and/or surfaces of spinal correction system 10. In some embodiments, the agent may include bone growth promoting material, such as, for example, bone graft to enhance fixation of the components and/or surfaces of spinal correction system 10 with vertebrae. In some embodiments, the agent may include one or a plurality of therapeutic agents and/or pharmacological agents for release, including sustained release, to treat, for example, pain, inflammation and degeneration.

Upon completion of a procedure, the surgical instruments and/or tools, assemblies and non-implanted components of spinal correction system 10 are removed and the incision(s) are closed. One or more of the components of spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10. In some embodiments, spinal correction system 10 may include one or a plurality of rods, plates, connectors and/or bone fasteners for use with a single vertebral level or a plurality of vertebral levels.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
a connector defining a longitudinal axis and extending between a first end and a second end, the connector comprising an opening extending through opposite uppermost and bottommost surfaces of the connector, the connector defining a cavity and including a member being selectively disposable in the opening such that a distal end of the member is positioned in the cavity;
a first longitudinal element being dynamically movable within the cavity and engageable with the member to limit movement in a first axial direction, the first longitudinal element being connectable with vertebral tissue; and
a second longitudinal element disposable within the cavity and connectable with vertebral tissue, the second longitudinal element being spaced apart from the first longitudinal element along the longitudinal axis,
wherein the first longitudinal element includes a first end fixed with at least one vertebra and a second end dynamically movable within the cavity.

2. A spinal construct as recited in claim 1, wherein the first longitudinal element includes a range of dynamic movement within the cavity in a second axial direction.

3. A spinal construct as recited in claim 1, wherein the first longitudinal element is dynamically rotatable within the cavity.

4. A spinal construct as recited in claim 1, wherein the first longitudinal element includes a range of dynamic movement in a second axial direction and dynamic rotation within the cavity.

5. A spinal construct as recited in claim 1, wherein the cavity comprises a longitudinal passageway.

6. A spinal construct as recited in claim 1, wherein the second longitudinal element includes a first end fixed with at least one vertebra and a second end dynamically movable within the cavity.

7. A spinal construct as recited in claim 1, wherein the second longitudinal element includes a first end fixed with at least one vertebra and a second end fixed with the connector.

8. A spinal construct as recited in claim 1, wherein the member includes a screw.

9. A spinal construct as recited in claim 1, wherein the second longitudinal element is fixed with the connector, the first longitudinal element being dynamically movable within the cavity and engageable with an end of the second longitudinal element to limit movement in the first axial direction.

10. A spinal construct as recited in claim 1, wherein the second longitudinal element is fixed with the connector, the first longitudinal element being dynamically movable within the cavity and engageable with the member to limit movement in the first axial direction.

11. A spinal construct comprising:
a connector defining a longitudinal axis and an axial passageway, the connector further defining at least five spaced apart threaded transverse openings that are each in communication with the passageway;
a member selectively disposable within one of the openings and in alignment with the cavity;
a first rod fixed with the connector and connectable with at least one vertebra; and
a second rod being dynamically movable within the cavity and engageable with an end of the first rod or the member to limit movement in a first axial direction, the second rod being connectable with at least one vertebra.

12. A method for treating a spine, the method comprising steps of:
providing the spinal construct recited in claim 1;
attaching the first longitudinal element with at least one vertebra;
connecting the first longitudinal element with the connector;
connecting the second longitudinal element with the connector and attaching the second longitudinal element with at least one vertebra; and
selectively disposing the member through the opening such that a distal end of the member is positioned in the cavity and that the second longitudinal element is dynamically movable within the cavity and engageable with the member to limit movement in a first axial direction.

13. A method for treating a spine as recited in claim 12, wherein the second longitudinal element has a range of dynamic movement within the cavity in a second axial direction.

14. A method for treating a spine as recited in claim 12, wherein the first longitudinal element is dynamically rotatable within the cavity.

15. A method for treating a spine as recited in claim 12, wherein the first longitudinal element includes a first end fixed with at least one vertebra and a second end dynamically movable within the cavity.

16. A method for treating a spine as recited in claim 12, wherein the first longitudinal element includes a first end fixed with at least one vertebra and a second end fixed with the connector.

17. A spinal construct comprising:
a connector defining a longitudinal axis and extending between a first end comprising a first threaded opening and a second end comprising a second threaded opening, the connector comprising a third threaded opening between the first and second openings, the connector defining a cavity and including a member being selectively disposable in one of the openings such that a distal end of the member is positioned in the cavity;
a first longitudinal element being dynamically movable within the cavity and engageable with the member to limit movement in a first axial direction, the first longitudinal element being connectable with vertebral tissue;
a second longitudinal element disposable within the cavity and connectable with vertebral tissue; and
a second member disposable in another one of the openings such that a distal end of the second member is positioned in the cavity and engages the second longitudinal element such that the second longitudinal element is movable in the first axial direction and is prevented from moving in an opposite second axial direction,
wherein the member has a maximum length that is less than that of the second member.

18. A spinal construct as recited in claim 17, wherein the member is engageable with the first longitudinal element to limit movement in an opposite second axial direction.

19. A spinal construct as recited in claim 17, wherein the openings each extend through opposite top and bottom surfaces of the connector.

* * * * *